United States Patent [19]

Kappel

[11] Patent Number: 5,675,848
[45] Date of Patent: Oct. 14, 1997

[54] INFLATABLE BLANKET HAVING PERFORATIONS OF DIFFERENT SIZES

[75] Inventor: Thomas F. Kappel, St. Louis, Mo.

[73] Assignee: Mallinckrodt Medical, Inc., St. Louis, Mo.

[21] Appl. No.: 544,501

[22] Filed: Oct. 18, 1995

[51] Int. Cl.$^6$ .................................................. A47C 31/10
[52] U.S. Cl. ............................ 5/482; 5/486; 5/502; 5/421
[58] Field of Search .................................. 5/468, 469, 482, 5/486, 423, 421; 607/96, 104, 107–111

[56] References Cited

U.S. PATENT DOCUMENTS

| | | |
|---|---|---|
| 630,565 | 8/1899 | Safran . |
| 1,291,191 | 1/1919 | Semple . |
| 1,590,522 | 6/1926 | Kalman . |
| 1,777,982 | 10/1930 | Popp . |
| 2,093,834 | 9/1937 | Gaugler . |
| 2,110,022 | 3/1938 | Kliesrath . |
| 2,122,964 | 7/1938 | Sweetland . |
| 2,235,966 | 3/1941 | Summers . |
| 2,512,559 | 6/1950 | Williams . |
| 2,601,189 | 6/1952 | Wales, Jr. . |
| 2,617,915 | 11/1952 | Blair . |
| 2,700,165 | 1/1955 | Talisman . |
| 2,706,988 | 4/1955 | Weber . |
| 2,791,168 | 5/1957 | Mauch . |
| 2,834,033 | 5/1958 | O'Brien .................... 5/502 |
| 2,998,817 | 9/1961 | Armstrong . |
| 3,034,132 | 5/1962 | Landsberger et al. . |
| 3,307,554 | 3/1967 | Thornton et al. . |
| 3,308,850 | 3/1967 | Gill . |
| 3,610,251 | 10/1971 | Sanderson . |
| 3,674,034 | 7/1972 | Hardy . |
| 3,740,777 | 6/1973 | Dee ......................... 5/469 |
| 3,757,366 | 9/1973 | Sacher . |
| 3,844,339 | 10/1974 | Kranz . |
| 4,026,299 | 5/1977 | Sauder . |
| 4,094,357 | 6/1978 | Sgroi . |
| 4,398,535 | 8/1983 | Guibert . |
| 4,457,295 | 7/1984 | Roehr . |
| 4,572,188 | 2/1986 | Augustine et al. . |
| 4,653,131 | 3/1987 | Diehl . |
| 4,660,388 | 4/1987 | Greene, Jr. ..................... 5/423 |
| 4,777,802 | 10/1988 | Feher . |
| 4,807,644 | 2/1989 | Sandhaus . |
| 4,867,230 | 9/1989 | Voss ........................... 5/469 |
| 4,959,877 | 10/1990 | Covil . |
| 4,997,230 | 3/1991 | Spitalnick ..................... 5/423 |
| 5,022,110 | 6/1991 | Stroh . |
| 5,044,364 | 9/1991 | Crowther . |
| 5,097,548 | 3/1992 | Heck et al. . |
| 5,106,373 | 4/1992 | Augustine et al. . |
| 5,125,238 | 6/1992 | Ragan et al. ..................... 5/423 |
| 5,165,400 | 11/1992 | Berke . |
| 5,184,612 | 2/1993 | Augustine ........................ 5/482 |
| 5,265,599 | 11/1993 | Stephenson et al. .............. 5/423 |
| 5,300,098 | 4/1994 | Philipot . |
| 5,300,100 | 4/1994 | Hickle . |
| 5,300,101 | 4/1994 | Augustine et al. . |
| 5,300,102 | 4/1994 | Augustine et al. . |
| 5,304,213 | 4/1994 | Berke et al. . |

(List continued on next page.)

FOREIGN PATENT DOCUMENTS

| | | |
|---|---|---|
| 1325484 | 12/1993 | Canada . |
| 0311336 | 4/1989 | European Pat. Off. . |
| 149244 | 11/1931 | Switzerland . |
| 85 03216 | 8/1985 | WIPO . |
| 94 03131 | 2/1994 | WIPO . |
| 95 20371 | 8/1995 | WIPO . |
| 95 35077 | 12/1995 | WIPO . |
| 96 03098 | 2/1996 | WIPO . |

*Primary Examiner*—Steven N. Meyers
*Assistant Examiner*—Tuyet-Phoung Pham
*Attorney, Agent, or Firm*—Rothwell, Figg, Ernst & Kurz, P.C.

[57] ABSTRACT

The present invention relates to blankets for use with forced air convection systems, wherein the blankets include perforations formed through the lower sheet of the blanket. In particular, the perforations are provided in a number of different sizes, such that a greater transfer of air may be provided in areas of the blanket which will directly cover portions of a patient.

9 Claims, 1 Drawing Sheet

U.S. PATENT DOCUMENTS

| | | |
|---|---|---|
| 5,304,217 | 4/1994 | Stephenson et al. . |
| 5,318,568 | 6/1994 | Kaufmann et al. . |
| 5,324,320 | 6/1994 | Augustine et al. . |
| 5,336,250 | 8/1994 | Augustine . |
| 5,343,579 | 9/1994 | Dickerhoff et al. ........................ 5/421 |
| 5,350,417 | 9/1994 | Augustine . |
| 5,360,439 | 11/1994 | Dickerhoff et al. . |
| 5,384,924 | 1/1995 | Dickerhoff et al. . |
| 5,392,847 | 2/1995 | Stephenson . |
| 5,405,370 | 4/1995 | Irani . |
| 5,405,371 | 4/1995 | Augustine et al. . |
| 5,408,712 | 4/1995 | Brun ............................................ 5/486 |
| 5,443,488 | 8/1995 | Namenye et al. . |

INFLATABLE BLANKET HAVING PERFORATIONS OF DIFFERENT SIZES

BACKGROUND

Hypothermia is a condition of subnormal body temperature and presents serious consequences to the patient suffering therefrom. It has been shown that nearly seventy five percent of all patients who undergo surgical procedures develop hypothermia. This equates to approximately fourteen million patients a year in the United States alone. The hypothermic condition is brought on by many factors including anesthesia, the air conditioning of the operating room, and the infusion of cold blood, I-V solutions, or irrigating fluids.

Several methods and products have been developed to help prevent hypothermia from occurring; such as the use of infrared lamps, cotton blankets, and warm water mattresses. However, none of these methods and products have proven completely successful. In fact, it has been shown that these methods and products can not even prevent the patients from losing their endogenous heat. (See Journal of Post Anesthesia Nursing, Vol. 5, No. 4, August 1990, pp 254–263).

Another method of helping to prevent hypothermia that has proven very effective is the use of forced warm air convection. As early as 1937, a refrigeration blanket using cold air convection was suggested in U.S. Pat. No. 2,093,834 to Gaugler. This blanket included a plurality of layers for channeling airflow from an inlet port. Non-inflatable portions were provided around the periphery of the blanket to secure the blanket around the body. Gaugler does not mention hypothermia treatment and does not suggest that the blanket could be used to supply warm air.

U.S. Pat. No. 2,512,559 to Williams also relates to a blanket for providing cooled air to a person. The blanket in Williams comprised a plurality of thin sheets of material connected together at a plurality of discrete locations and connected together in a continuous line about the peripheral edge. An air inlet was provided to communicate with space between the sheets to allow cool air to be supplied thereto. Again, no mention of hypothermia treatment or the supply of warm air is made.

In U.S. Pat. No. 4,572,188 to Augustine, et al., a forced air convection system which can supply either cool or warm air to a blanket is described. The blanket in Augustine, et al. comprises a plurality of inflatable hollow tubes having their interiors connected together through transverse openings. An entry port is provided in the upper surface of the blanket for admitting the cool or warm air and small exit ports are provided through the lower surface to allow the cool or warm air to flow out toward a body covered by the blanket.

Other patents relating to the supply of cool or warm air to a person through an inflatable blanket include U.S. Pat. Nos. 4,660,388 to Greene, Jr.; 4,777,802 to Feher; and 4,867,230 to Voss; 5,125,238 to Ragan et al; 5,300,100 to Hickle et al; 5,300,102 to Augustine et al; 5,324,320 to Augustine et al; 5,343,579 to Dickerhoff et al; 5,360,439 to Dickerhoff et al; and 5,384,924 to Dickerhoff et al. Each of these patents describe blankets having various attributes and configurations to supply cool or warm air to the person.

While there are a number of patents noted above and others not mentioned which relate to inflatable blankets for use in supplying cool or warm air to a patient, there remains a need in the art for improvements to forced air convection systems.

OBJECTS OF THE INVENTION

It is one object of the present invention to provide a blanket for a forced air convection system which allows the greatest transfer of heated or cooled air to be directed to selected portions of the patient.

SUMMARY OF THE INVENTION

The above object and others are accomplished according to the present invention by providing a blanket for a forced air convective system which includes exit perforations having different sizes.

DETAILED DESCRIPTION OF THE INVENTION

Figure 1:
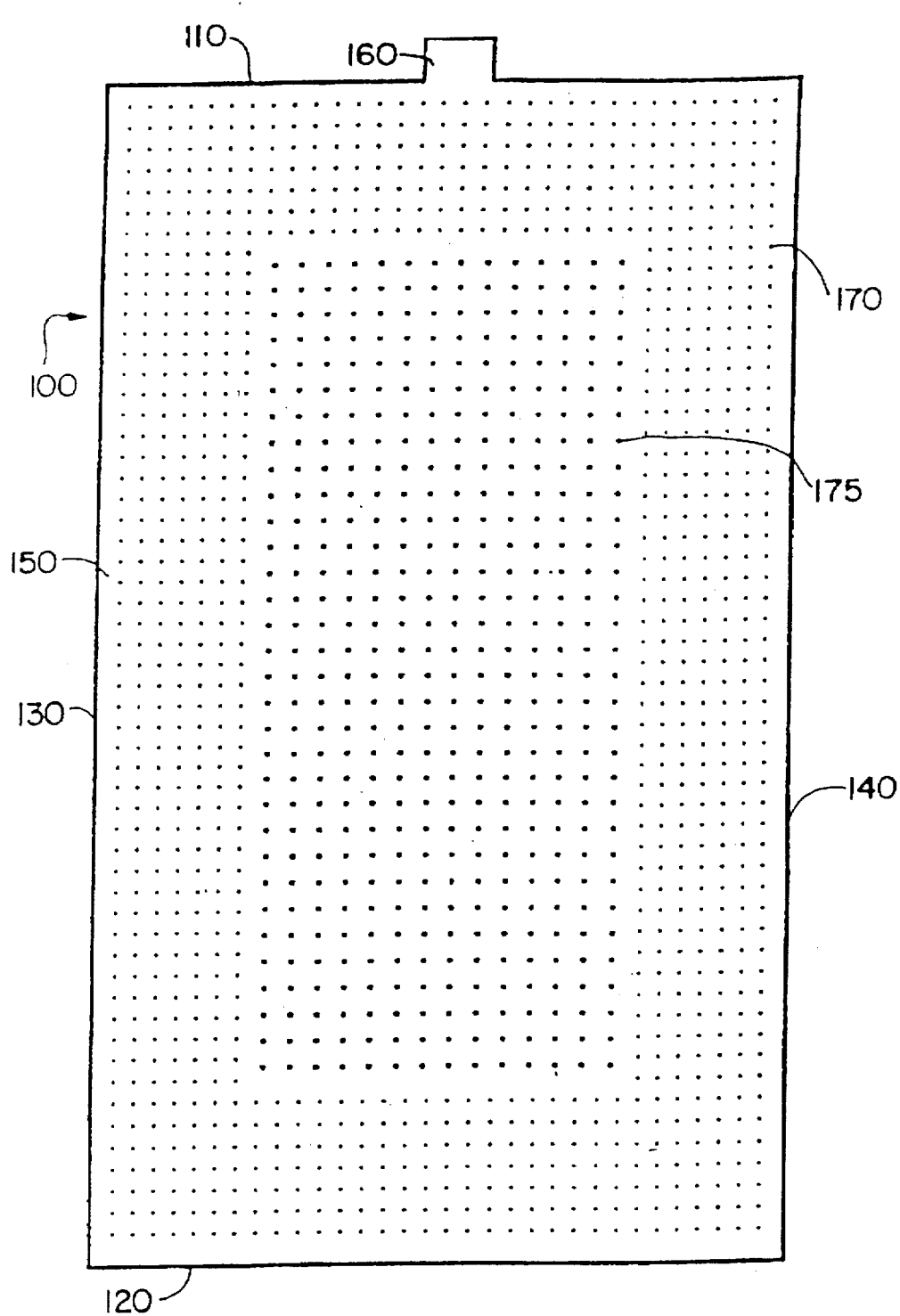
FIG. 1 is a plan view of a blanket for a forced air convection system according to one embodiment of the present invention.
Figure 2:
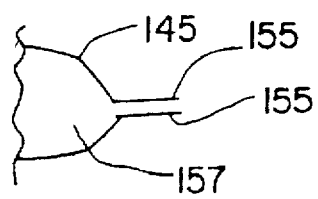
FIG. 2 is a schematic side view, with portions broken away, of a blanket in accordance with the invention.

FIG. 1 is a plan view of a blanket, generally designated by reference numeral 100, for a forced air convection system, according to one embodiment of the present invention. In particular, blanket 100, includes an upper or head end 110, a lower or foot end 120, and two sides 130, 140. The blanket 100, further includes an upper sheet of material 145, and a lower sheet of material 150. The upper sheet and lower sheet 150, are sealed together around respective peripheral edges 155 to form a cavity 157 therebetween, which may be inflated by introduction of air from an appropriate source. The upper sheet and lower sheet 150, may further be connected together in any one of several desirable configurations, such as spot welds, interconnected columns, interconnected tubes, etc. The blanket 100, includes at least one inlet port 160, for attachment to a source of forced air which will be used to inflate the blanket 100, and provide either warming or cooling air to the patient. As shown in FIG. 1, the inlet port 160, is formed along one end of the blanket 100. However, other configurations are equally acceptable and are within the scope of the present invention, as will be further discussed below. The lower sheet of the blanket 100, includes a plurality of perforations or small exit holes 170, 175, formed therethrough which allow air to escape from the blanket 100, toward a patient.

It is desirable to provide the greatest transfer of heated or cooled area to the trunk of the patient. Therefore, as shown in FIG. 1, the perforations 170, provided over a middle portion of the blanket 100, have a larger size than perforations 175, provided in peripheral areas of the blanket 100. In one particular embodiment of the present invention, the larger perforations 170, are arranged in the general shape of a patient's body.

The large perforations according to the present invention preferably have a diameter in the range of 0.075 to 0.150 inches. The small perforations according to the present invention preferably have a diameter in the range of 0.058 to 0.116 inches.

The present invention relates to any number of patterns of large and small perforations. For example, the large perforations may be provided only over the chest area of a patient, or over a particular area of a patient to which it is desired to provide greater transfer of heated or cooled air. In addition, the large perforations may be provided in more than one area, to produce additional areas of more efficient transfer of heated or cooled air.

In addition, more than two sizes of perforations may be provided. The largest perforations would be used in those areas where the greatest transfer of heated or cooled air is desired, and the smallest perforations would be used in those areas where the least transfer of heated or cooled air is desired. Perforations having an intermediate size or several intermediate sizes can be provided in other areas of the blanket. In particular, this intermediate perforations may be provided in areas between the large and small perforations so as to create a gradient of air transfer across the blanket.

By providing the pattern of large and small perforations, it is possible to provide heating or cooling to a patient in a more efficient manner. In particular, the large perforations provide greater transfer of heated or cooled air directly to the patient, while small perforations are used in the peripheral areas of the blanket not directly covering a patient. Providing the patterned large and small perforations in accordance with the present invention assures that the greatest amount of heating or cooling air will be provided directly to the patient.

The blanket shown in FIGS. 1 represents full body blankets but the present invention would be equally applicable to blankets intended to cover only portions of the patient, such as an upper body blanket or a lower body blanket. The blankets according to the present invention are also equally useful in both adult and pediatric sizes. Additionally, the blankets according to the present invention may be used equally effectively in either the operating room or in other areas of the hospital, such as the PACU. Moreover, as noted, the blankets according to the present invention may be used to provide either warming or cooling to a patient.

As noted above, the inlet port as shown in FIG. 1, is located along an edge of the blanket. However, the inlet port may be located at almost any position which allows the blanket to be easily inflated. For example, the inlet port may be provided along any edge of the blanket, at a corner of the blanket or through the upper or lower sheet of the blanket at a location spaced away from the edge of the blanket. In addition, multiple inlet ports may be provided to increase the versatility of the blanket.

The blankets of the present invention may be formed of any suitable material capable of being sealed together at selected positions and having sufficient strength to allow inflation and adequate air distribution within the inflated portion. Such materials include plastics, non-woven wood pulp compositions, laminated plastic and wood pulp materials, and combinations thereof.

The foregoing has been a description of certain preferred embodiments of the present invention, but is not intended to limit the invention in any way. Rather, many modifications, variations and changes in details may be made within the scope of the present invention.

What is claimed is:

1. An inflatable blanket for a forced air convection system comprising:

an upper sheet of material having a generally rectangular shape with an upper end, a lower end and two sides;

a lower sheet of material having a generally rectangular shape with an upper end, a lower end and two sides;

wherein said upper sheet and said lower sheet are sealed together around their peripheral edges at their respective upper ends, lower ends and sides, to create an inflatable cavity having an upper end, a lower end, and two sides therebetween;

an inflation port connected to said inflatable cavity through which inflation medium may be introduced to said inflatable cavity to inflate said blanket; and a plurality of perforations formed through said lower sheet, wherein said perforations are provided as a first area of large perforations in said lower sheet, which first area is at least substantially surrounded by a plurality of smaller perforations.

2. A blanket according to claim 1, wherein said large perforations are provided in said first area for positioning directly over a patient's body and said small perforations are provided in areas peripheral to the first area where said larger perforations are provided.

3. A blanket according to claim 1, wherein said large perforations have a diameter in the range of 0.075 to 0.150 inches and said small perforations have a diameter in the range of 0.058 to 0.116 inches.

4. A blanket according to claim 1, wherein said large perforations are provided in said first area for covering a chest of a patient and said small perforations are provided in areas peripheral to the first area where said larger perforations are provided.

5. A blanket according to claim 1, wherein large perforations are provided in more than one area of said blanket and small perforations are provided in areas peripheral to the areas where said large perforations are provided.

6. A blanket according to claim 1, wherein said perforations are provided in two different sizes.

7. A blanket according to claim 1, wherein said perforations are provided in three or more different sizes.

8. A blanket according to claim 7, wherein said perforations of different sizes are arranged in a pattern which provides a gradient of air transfer across said blanket.

9. A blanket according to claim 1, wherein said first area of large perforations is completely surrounded by said small perforations.

* * * * *

UNITED STATES PATENT AND TRADEMARK OFFICE
Certificate

Patent No. 5,675,848                                                    Patented: October 14, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Thomas F. Kappel, St. Louis, MO; Scott D. Dickerhoff, Ballwin, MO; and Dennis S. Chivetta, Ballwin, MO.

Signed and Sealed this Twenty-sixth Day of August 2003.

<div style="text-align:right">

KATHERINE MATECKI
*Supervisory Patent Examiner*
Art Unit 3627

</div>